United States Patent [19]

Näder et al.

[11] 4,310,932
[45] Jan. 19, 1982

[54] ARTIFICIAL KNEE-JOINT

[76] Inventors: Max Näder, Hindenburgring 39, 3428 Duderstadt; Richard Glabiszewski, Im Puttfeld 1, 3428 Duderstadt 13, both of Fed. Rep. of Germany

[21] Appl. No.: 78,934

[22] Filed: Sep. 26, 1979

[30] Foreign Application Priority Data

Sep. 27, 1978 [DE] Fed. Rep. of Germany ....... 2841999

[51] Int. Cl.³ .............................................. A61F 1/08
[52] U.S. Cl. ............................................... 3/28; 3/22
[58] Field of Search ....................................... 3/22–29, 3/2

[56] References Cited

U.S. PATENT DOCUMENTS

| | | | |
|---|---|---|---|
| 2,208,275 | 7/1940 | McCann | 3/29 |
| 2,533,008 | 12/1950 | Hanson | 3/27 X |
| 3,823,424 | 7/1974 | May | 3/22 |
| 4,064,569 | 12/1977 | Campbell | 3/26 |
| 4,145,766 | 3/1979 | May | 3/22 X |
| 4,152,787 | 5/1979 | Meggyesy | 3/27 |

FOREIGN PATENT DOCUMENTS

| | | | |
|---|---|---|---|
| 897811 | 5/1962 | United Kingdom | 3/27 |
| 1247851 | 9/1971 | United Kingdom | 3/22 |
| 1533796 | 11/1978 | United Kingdom | 3/22 |

Primary Examiner—Clifford D. Crowder
Attorney, Agent, or Firm—Michael J. Striker

[57] ABSTRACT

The artificial knee joint for an artificial leg includes a pair of substantially parallel pivotable bars which are connected by pivoting joints to an upper part and a lower part of the knee joint, respectively. One of the bars is anterior and the other is posterior with respect to a position of the artificial leg. The upper part has two spaced pivoting joints and the lower part has two spaced pivoting joints. The imaginary connecting line between the pivoting joint of the anterior bar and the pivoting joint of the posterior bar is substantially horizontal when the leg is in its vertical position. The imaginary connecting line between two pivoting joints of the anterior bar is inclined at a small angle to the imaginary connecting line between two pivoting joints of the posterior bar.

23 Claims, 4 Drawing Figures

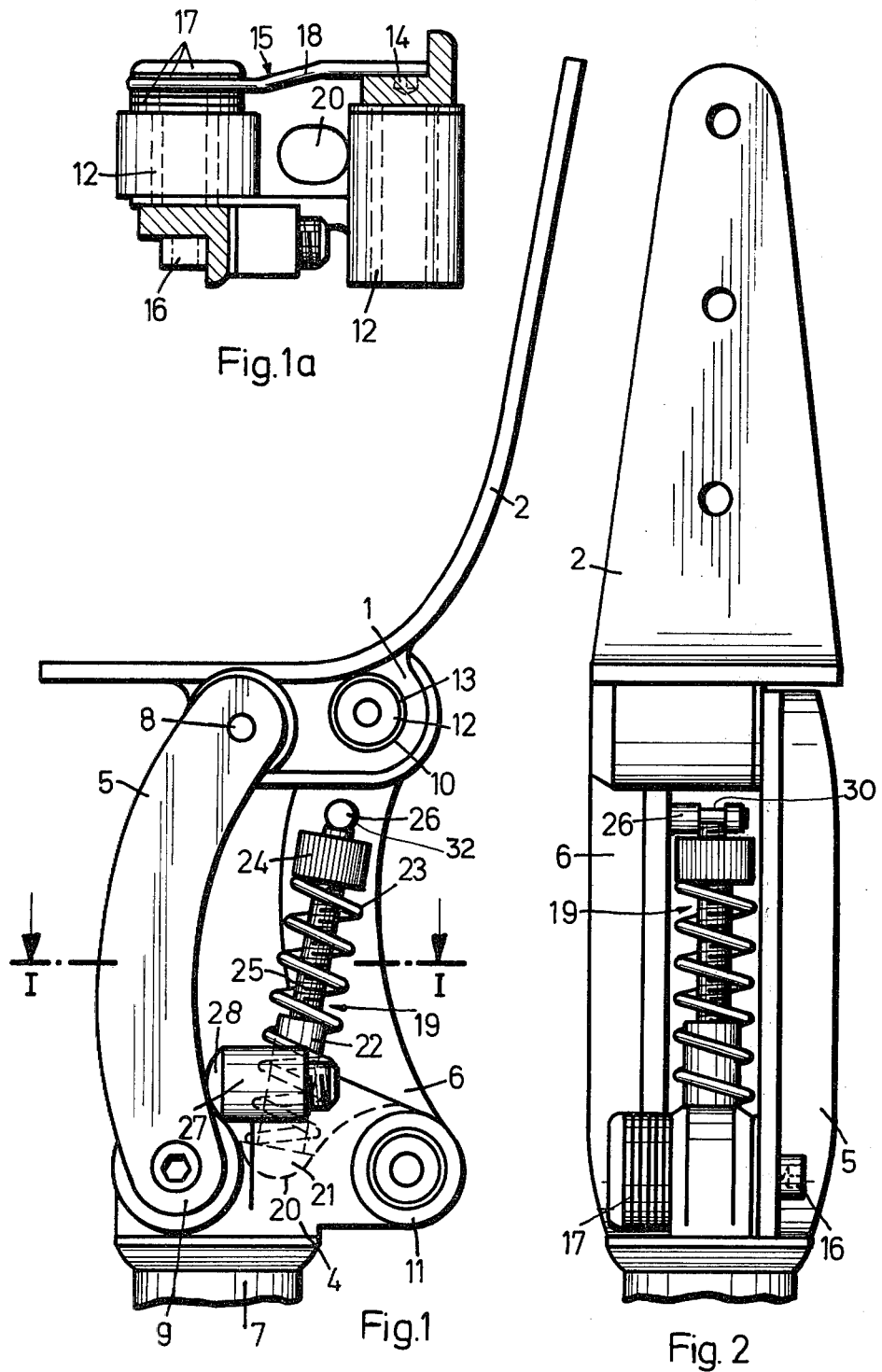

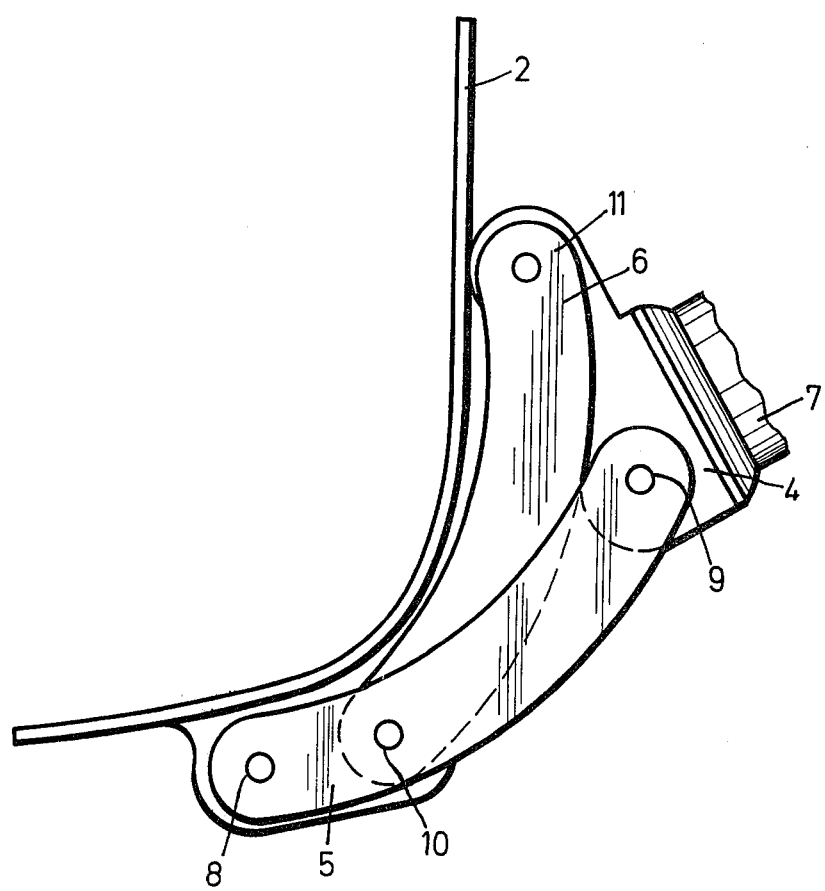

ARTIFICIAL KNEE-JOINT

BACKGROUND OF THE INVENTION

The invention relates to an artificial knee joint with one upper and one lower joint part, each of which having an anterior and a posterior pivoting joint of which the two respective anterior and posterior pivoting joints are connected by linking bars of a rearward curvature.

Such knee joints are classified as four-axes joints already known per se for several decades. The newer joints of this type have the advantage that they can also be used with exarticulate amputations, i.e. amputations in which the upper thigh remains virtually complete and severance is made by removal of the complete lower thigh. A knee joint of this type is known from the DE Publication of Specifications No. 23 32 993. The connection between the upper joint part and the lower joint part is effected by two pairs of link bars joined by axles at their respective ends. The position of the pivoting joint is determined by complicated angular relations which must be adhered to with greatest precision in order to ensure good functioning of the joint. The two anterior link bars connecting the two anterior pivoting joints, are designed very short when compared to the posterior link bars and have a considerably stronger curvature. The two anterior pivoting joints are therefore located relatively close to each other, while the distance between the posterior pivoting joints is approximately twice as much.

The functioning of this known knee joint cannot be faulted per se, since it ensures a sufficient stability of standing with the leg extended and a good location of the pivot within the needs for bending. The movement of the natural knee can be approximated with this joint relatively well.

It is to be considered a disadvantage of the joint as known, that a multitude of parts of complicated shapes is required for the construction of the knee joint. In consequence thereof, fitting of the knee joint is expensive. A further disadvantage can be seen in the fact that a relatively large space is required for the knee joint, resulting in the necessity of making relatively thin the customarily-used cosmetic covering, which will therefore not be of a perfect appearance and furthermore will be chafed through at a faster rate.

Contrarywise, the invention is based upon the task of creating an artificial knee joint of the type previously mentioned, with its construction being less complicated and having a lower spatial requirement.

As per invention, this task is solved by the connection between the upper and lower joint part being formed by two link bars arranged at both sides of the center of the joint, by the lines connecting the two anterior joints on one side and the two posterior joints on the other, having a relative inclination at a small angle, and by the line connecting the two pivoting joints of the lower part being approximately horizontal.

Contrary to the knee joint as known, two link bars will suffice for the knee joint as per invention. Arranging the pivoting joints as per invention, allows these to be positioned close to each other, so that merely small lever forces will occur that have to be absorbed by the link bars.

The components required for the knee joint as per invention may be of simple design and can therefore easily be produced. The entire knee joint will therefore require less space in all three directions than joints known heretofore.

The advantages of manufacture may be enlarged further by both link bars being of the same shape. They may then preferably consist of identical parts inserted into the knee joint at an offset of 180° relative to each other, plus or minus, respectively, the acute angle. The link bars will then preferably be in the shape of a circular segment, whilst with the knee joint as known, different link bars were inserted anterior and posterior, this being considered absolutely necessary. The knee joint as per invention allows the use of anterior and posterior of two completely identical link bars.

The manufacture of the knee joint can therefore further be simplified without having to make any compromises in the function of the knee joint.

It has been shown of particular advantage herein if the lines connecting the two pivoting joints of the lower joint part on one side, and the two posterior pivoting joints on the other, are standing at approximately a right angle to each other. It has proved in practice, to dimension the distances between the two pivoting joints of the upper joint part, between the two pivoting joints of the lower joint part, and between the two posterior pivoting joints at a ratio of approximately 1:2:4.

A further essential simplification of the installation of the knee joint can be reached by the link bars being inserted into corresponding bores of the joint parts by dowels fitting therein. This obviates the necessity of having an individual screw for every pivoting joint.

A particularly stable design is attained when the link bars are constructed from an angle shape.

The dowels can preferably be made hollow so that the pins of a locking element can be inserted. In this way, an extremely simple locking of the entire knee arrangement can be made by means of one single screw when the pins of a locking element are inserted within the two dowels inserted into the lower joint part, with one of the locking pins protruding through the pivoting joint screwed into the locking element. The entire arrangement can therefore be held together by the screw threaded into the locking element, wherein the locking element prevents the two lower dowels from sliding out of the respective bore and wherein the alternating attachment of both link bars will cause the upper dowels being automatically retained together by the lower dowel without a special additional fastener being required for the former.

In a preferred embodiment, the locking element is joined secure against rotation to the dowel the screw. Herein, the locking element may preferably be provided with a friction brake on its end having the screw. In this way, the function of the one screw which holds the entire arrangement, can further be extended, so that the ease of movement can be regulated with it. The knee will execute a swinging movement more or less retarded, depending upon the adjustment of the screw.

In a particularly simple embodiment, the friction brake is formed by a stack of circular discs through which the screw protrudes. Herein, the discs may alternatingly be made of metal and of plastic.

The design of the knee joint as per invention, particularly the use of only two link bars, allows the space-saving accommodation of a spring element necessary for the regulation of the ease of movement. Preferably, this element will be clamped between the posterior link bar and the lower joint part. The pretensioning of the spring elements can be adjusted herein by a stop pin for the helical spring being screwed onto a thread.

The lower joint part may be provided with a stop limiting the rearward movement of the anterior link bar. In a simple embodiment, this stop is preferably adjustable by having a threaded projection with which it is screwed into a threaded bore of the lower joint part.

The complete knee joint, including all components required to regulate the ease of movement, can therefore be accommodated within a minimal space, since all components provided to regulate the ease of movement can be arranged within the space between the two link bars. Herein lies a considerable advantage versus all known knee joints of the type under discussion.

The invention is to be explained more closely below, with the aid of an embodiment shown in a drawing.

BRIEF DESCRIPTION OF THE DRAWINGS

FIG. 1 is the side view of a knee joint as per invention;

FIG. 1a is a section along the line I—I;

FIG. 2 is a front view of the knee joint as per FIG. 1;

FIG. 3 is the position of the link bars with the knee joint bent.

DETAILED DESCRIPTION OF THE PREFERRED EMBODIMENTS

The knee joint shown in FIGS. 1 to 3 consists of one upper joint part which is integrally connected to an approximately L-shaped retaining anchor 2 for joining to a stump stem (not shown). The upper joint part 1 is connected with the lower joint part 4 by two link bars 5, 6. The lower thigh tube 7 of a prosthetic lower thigh is attached to the lower joint 4.

The link bar 5, anterior when viewed in the direction of walking, is connected to the upper joint part 1 by a pivoting joint 8 and to the lower joint part 4 by a pivoting joint 9. Two further pivoting joints 10, 11 connected by the posterior link bar 6 are arranged behind these two pivoting joints 8, 9.

The link bars 5 and 6 are both of identical shape and represent a circular segment bent rearwards. They are constructed from an angle shape affording them a particular rigidity. Viewed from front, the two link bars are each on different sides of the center of the knee joint. The pivoting joints 8, 9, 10, 11 are formed by the dowels 12 which are fitted into corresponding bores of the joint parts 1, 4.

The pivoting joints 9, 11 in the lower joint part 4, are in horizontal juxtaposition when viewed with the lower thigh tube 7 standing vertical.

The imaginary line connecting the centers of pivoting joints 9, 11 stands substantially perpendicular to the imaginary line connecting the centers of posterior pivoting joints 10, 11. The imaginary line connecting the centers of two anterior pivoting joints extends at a small angle α to the vertical, it is thus inclined at the angle α to the imaginary line connecting the centers of two posterior joints.

It follows therefrom that the distance between the two pivoting joints 8, 10 in the upper joint part 1 is smaller than the distance between the two pivoting joints 9, 11 in the lower joint part 4. In the embodiment shown, the distance between the upper pivoting joints 8, 10 is approximately 2 cm, the distance between the two lower pivoting joints 9, 11 approximately 4 cm, and the distance between the two posterior pivoting joints 10, 11 about 8 cm. With this arrangement, the virtual pivot of the knee joint corresponding to a crossing point of the axes of the thigh and the shank is located anatomically correct within the knee. It will not change its position essentially, even when the knee is bent. On such bending, the knee joint will effect an anatomically correct shortening of the leg, so that sufficient freedom is given for the prosthetic foot and the wearer of these prosthetics may walk unencumbered.

The dowels 12 are constructed as hollow dowels into which the pins 14 of a locking element 15 can be inserted. The locking element 15 engages the two dowels 12 in the lower joint part 4 by means of a short pin 14 in the posterior pivoting joint, and engaging the anterior pivoting joint 9 by means of a pin designed as a screw 16 which, protruding through the link bar 5 and the dowel 12, is screwed into the locking element 15. This screw is the sole means of fastening for all pivoting joints 8, 9, 10, 11. Simultaneously, the screw 16 is also used for adjustment of the friction of the axle, with the locking element 15 being constructed as friction brake. At its end accommodating the screw 16, the locking element 15 consists of a stack of circular friction discs 17 (FIG. 1a) made alternatingly of metal and plastic. The metallic discs are so linked that rotation is precluded, except for that disc linked the spring strap 18 of the locking element 15 holding the short pin 14, while the plastic discs can rotate freely. The linking between the metallic discs precluding rotation is effected by the outermost metallic disc having a rectangular projection (not shown) fitting into a corresponding recess provided the dowel 12 of the pivoting joint 9. The other metallic discs have a corresponding rectangular recess (not shown). The thread for holding the screw 16 is also located within the rectangular projection. Upon rotation of the pivoting joint 9, every metallic disc will in this manner interact with a plastic disc as friction surface. Depending upon the strength of the pressure exerted by the screw 16, friction may be higher or lower so that adjusting of the screw 16 affects the friction between the discs 17 and thus allows regulation of the swinging movement of the lower thigh.

For returning the lower thigh when it is bent backwards with respect to the upper thigh during walking, knee joints are provided with a spring element 19 or so-called forwardhauling spring to bring the shank into the forward position. The forward-hauling spring is known in the constructions of the foregoing type.

In the embodiment shown, the latter is clamped between the posterior link bar 6 and the lower joint part 4. The lower joint part 4 has for this purpose a socket 20 between the pivoting joints 9, 11 serving to hold a correspondingly shaped plastic ball 21 at the end of a plastic cylinder 22. The plastic ball serves as a stop for a coil spring 23 which at its other end is retained by a stop pin 24 which can be adjusted as to position along a threaded rod 25. The threaded rod 25 is movably held in the plastic cylinder 22. A bore at the posterior link bar 6 is provided for the insertion of a pin 26 which has a wide groove 30 serving as abutment for the spring element 19. For this purpose, the end of the threaded rod 25 has a cylindrical recess 32 which partially surrounds the pin 26. The spring element is compressed on bending the knee. By this, it will exert a multiplied returning force which, on walking will press the lower thigh forward. The arrangement of the pivots ensures that upon full bending back of the knee, the spring force is not acting any longer in the direction of extending the knee but, on the contrary, will support the full bending back of the knee. In this way, the knee, when fully bent back, can be kept in a resting position. The returning force of the forward-hauling spring can be adjusted to the individual circumstances of the prosthetics wearer with the aid of an adjustable stop pin 24. As can be seen from FIG. 1, the lower joint part 4 has an upward strap 27 with a threaded bore. A stop 28 is screwed into the threaded bore by means of a threaded projection.

The stop 28 is pointing forward, so that it will delimit the rearward movement of the anterior link bar 5. By constructing the stop 28 with a threaded projection, its position can be varied, so that also the resting position of the knee joint with a leg extended can be adjusted in such a manner that the inclination of the retaining anchor 2 and thus also of the stump of the upper thigh when the knee joint is extended, will depend upon the setting of the stop 28.

Thus, all parts essential for the function of the knee joint are located in the space defined vertically by the upper joint part 1 and the lower joint part 4 and horizontally by the two link bars 5, 6. The knee joint as per invention consists of very few components all of simple shape, allowing easy installation. By reason of the compact construction, a cosmetic cover can be applied in the required thickness, affording a faultless esthetic appearance.

We claim:

1. An artificial knee joint for an artificial leg, comprising an upper joint part including an anterior pivoting joint and a posterior pivoting joint spaced from each other; a lower joint part also including an anterior pivoting joint and a posterior pivoting joint spaced from one another; a pivotable anterior connecting bar interconnected between the anterior pivoting joint of said upper part and the anterior pivoting joint of said lower part; and a pivotable posterior connecting bar interconnected between the posterior pivoting joint of said upper part and the posterior pivoting joint of said lower part, the imaginary connecting line extending between the anterior pivoting joint of said lower part and the posterior pivoting joint of said lower part being substantially horizontal when the leg is in a vertical position, and the imaginary connecting line extending between the anterior pivoting joint of said upper part and the anterior pivoting joint of said lower part being inclined at a relatively small angle relative to the imaginary connecting line extending between the posterior pivoting joint of said upper part and the posterior pivoting joint of said lower part.

2. The joint of claim 1, wherein the ratio between the distance between the anterior pivoting joint and the posterior pivoting joint of said upper part and the distance between the anterior pivoting joint and the posterior pivoting joint of said lower part and the distance between the posterior pivoting joint of said upper part and the posterior pivoting joint of said lower part is approximately 1:2:4.

3. The joint of claim 1, wherein said anterior connecting bar and said posterior connecting bar are of the identical shape.

4. The joint of claim 3, wherein said connecting bars are inserted into the knee joint substantially at an angle of 180° relative to each other with addition or subtraction of said small angle.

5. The joint of claim 4, wherein the imaginary connecting line extending between the anterior pivoting joint and the posterior pivoting joint of said lower part is substantially perpendicular to the imaginary connecting line extending between the posterior pivoting joint of said upper part and the posterior pivoting joint of said lower part.

6. The joint of claim 5, wherein said connecting bars each has an angular shape.

7. The joint of claim 5, wherein said connecting bars each has a shape of a circular segment.

8. The joint of claim 7, wherein said upper and said lower parts each has two bores spaced from each other and each of said pivoting joints includes a dowel fitted into a respective bore of said lower and upper joint parts.

9. The joint of claim 8, wherein each of said dowels is hollow.

10. The joint of claim 9, wherein each of said pivoting joints further includes a pin connected to a respective bar and insertable into a respective dowel.

11. The joint of claim 10, further including a locking element interconnected between the dowels of the anterior pivoting joint and the posterior pivoting joint of said lower joint part.

12. The joint of claim 11, wherein the pin insertable into the dowel of the anterior pivoting joint is a screw secured on said dowel against rotation.

13. The joint of claim 12, further including a friction brake arranged at one end of said screw.

14. The joint of claim 13, wherein said friction brake includes a plurality of friction discs outwardly extending from the dowel of said anterior pivoting joint of said lower joint part.

15. The joint of claim 14, wherein at least two of said discs are secured on the dowel of said anterior pivoting joint of said lower part against rotation.

16. The joint of claim 15, wherein said friction discs are alternately arranged discs of metal and plastic.

17. The joint of claim 16, further including a spring element clamped between said lower joint part and said posterior connecting bar.

18. The joint of claim 17, wherein said spring element is a helical spring.

19. The joint of claim 18, wherein said spring is pretensioned and wherein means for adjusting the position of said spring between said lower joint part and said posterior connecting bar are provided.

20. The joint of claim 19, wherein said adjusting means includes a bolt supporting said spring and having a thread and a stop pin threadably adjustable along the thread of said bolt and retaining said spring.

21. The joint of claim 20, further including a stop mounted on said lower joint part and operative for delimiting the rearward movement of said anterior connecting bar.

22. The joint of claim 21, wherein said stop is adjustable.

23. The joint of claim 22, wherein said stop has a projection with an external thread, said lower joint part having a threaded bore receiving said projection.

* * * * *